(12) United States Patent
Jonsson

(10) Patent No.: US 6,871,996 B2
(45) Date of Patent: Mar. 29, 2005

(54) DEVICE AT MIXING DEVICES FOR MIXING PULVERULENT AND LIQUID SUBSTANCES WITH EACH OTHER FOR THE MANUFACTURE OF MEDICAL PRODUCTS

(75) Inventor: Ernst Jonsson, Lund (SE)

(73) Assignee: Biomet Merck Cementing Technologies AB, Sjobo (SE)

(*) Notice: Subject to any disclaimer, the term of this patent is extended or adjusted under 35 U.S.C. 154(b) by 114 days.

(21) Appl. No.: 10/281,545

(22) Filed: Oct. 28, 2002

(65) Prior Publication Data

US 2003/0086332 A1 May 8, 2003

(30) Foreign Application Priority Data

Nov. 7, 2001 (SE) .............................................. 0103689

(51) Int. Cl.[7] ................................................ B01F 13/06
(52) U.S. Cl. ........................ 366/139; 366/256; 366/332; 222/246
(58) Field of Search ................................. 366/130, 139, 366/256, 332, 333; 206/219–222; 222/243, 246

(56) References Cited

U.S. PATENT DOCUMENTS

| | | |
|---|---|---|
| 3,752,604 A | 8/1973 | Dorn |
| 5,058,770 A | 10/1991 | Herold et al. |
| 5,328,262 A | 7/1994 | Lidgren et al. |
| 5,501,520 A * | 3/1996 | Lidgren et al. ............. 366/139 |
| 5,549,380 A | 8/1996 | Lidgren et al. |
| 5,551,778 A | 9/1996 | Hauke et al. |
| 5,788,463 A | 8/1998 | Chan |

* cited by examiner

*Primary Examiner*—David Sorkin
(74) *Attorney, Agent, or Firm*—Tarolli, Sundheim, Covell & Tummino L.L.P.

(57) ABSTRACT

The present invention relates to a device at mixing devices for mixing pulverulent and liquid substances with each other for the manufacture of medical products, wherein a displaceable piston means (17) has at least one groove (22) extending around said piston means (17) and at least one sealing ring (23) is located in said groove (22). At least one connecting passage (22e) is provided for preventing a liquid substance (21) from generating or building up such a pressure in an inner space (22d) in the groove (22) within or behind the sealing ring (23) that said pressure presses the sealing ring (23) in a direction outwards (F) relative to the groove (22) towards a surrounding wall (1a) of the mixing device (1) and prevents or counteracts flow of the liquid substance (21) past the piston means (17) when said piston means (17) is displaced.

14 Claims, 2 Drawing Sheets

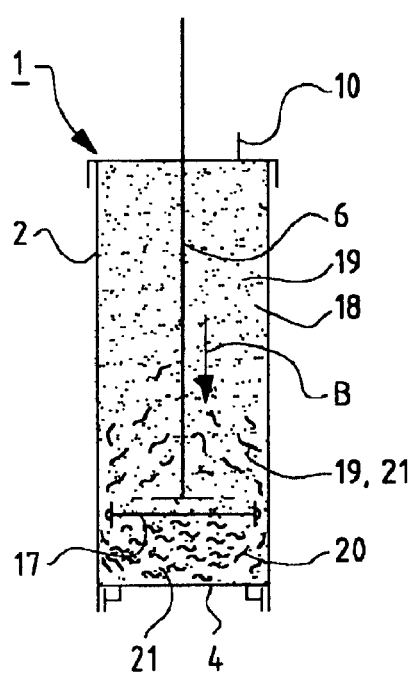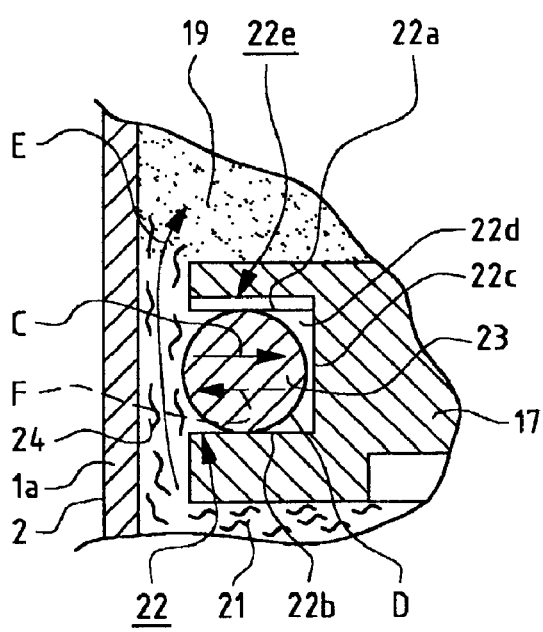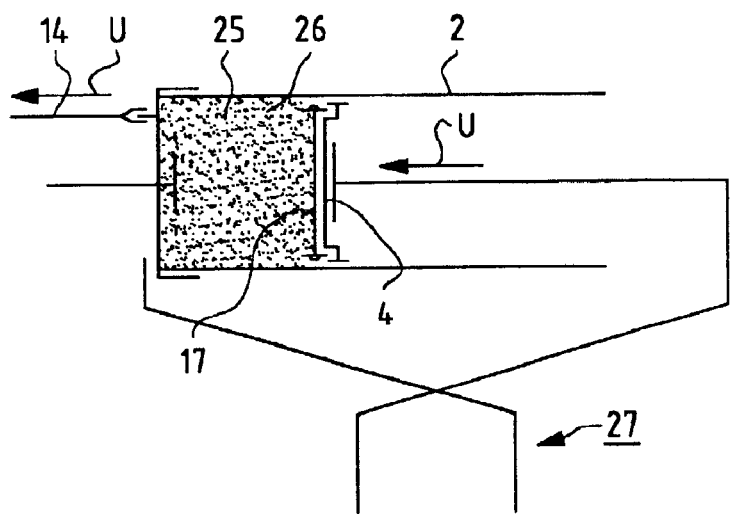

US 6,871,996 B2

DEVICE AT MIXING DEVICES FOR MIXING PULVERULENT AND LIQUID SUBSTANCES WITH EACH OTHER FOR THE MANUFACTURE OF MEDICAL PRODUCTS

FIELD OF THE INVENTION

The present invention relates to a device at mixing devices for mixing pulverulent and liquid substances with each other for the manufacture of medical products. The pulverulent substance is provided in a first space on one side of a displaceably mounted piston means and the liquid substance in a second space on the opposite side of said piston means. The piston means is displaceable by a displacement means. The piston means has at least one groove extending around said piston means, at least one sealing ring being located in said groove. The sealing ring is provided to cooperate, in a sealing position, with the piston means and with a wall of the mixing device surrounding said piston means, whereby the piston means and sealing ring sealingly separate the first and second spaces from each other for prevent the pulverulent substance and the liquid substance from mixing with each other when mixing should not occur. The sealing ring is provided, when loaded by the liquid substance during displacement of the piston means in a direction towards the second space containing the liquid, to be pressed inwards in the groove by the liquid substance and thereby at least partially being brought to leave its sealing position such that the liquid substance may flow into the first space containing the pulverulent substance for mixing therewith.

BACKGROUND OF THE INVENTION

Mixing devices for mixing a pulverulent polymer and a liquid monomer for the manufacture of bone cement are previously known from U.S. Pat. No. 5,328,262 and U.S. Pat. No. 5,551,778. In the embodiment of U.S. Pat. No. 5,551,778, the liquid substance—here a monomer—is located in a closed container. This container is placed in a mixing chamber in which a pulverulent substance—here a polymer—is also located. The container with the liquid substance is opened by penetrating the wall thereof, whereby the liquid and pulverulent substances come in contact with each other and may be mixed with each other.

SUMMARY OF THE INVENTION

The object of the present invention has been to present a device in which the liquid and pulverulent substances can be placed in two spaces which are separated from each other by a piston means having a sealing ring, and this is arrived at according to the invention by means of the characterizing features of primarily subsequent claim 1.

Since the invention has said characterizing features, it is achieved that the liquid and pulverulent substances can be located on opposite sides of a piston means having a sealing ring which has an effective sealing capacity when required and an effective transmitting or permeable capacity when this is required.

BRIEF DESCRIPTION OF THE DRAWINGS

The invention will be further described below with reference to the accompanying drawings, in which:

FIG. 2 schematically shows the mixing device of FIG. 1 during displacement of a piston means forming part thereof;

FIG. 3 is a generous magnification of parts of the piston means and surrounding members of the mixing device of FIG. 2; and FIG. 4 illustrates the mixing device of FIG. 1 when bone cement is fed out of said mixing device.

DETAILED DESCRIPTION OF THE INVENTION

Figure 1:
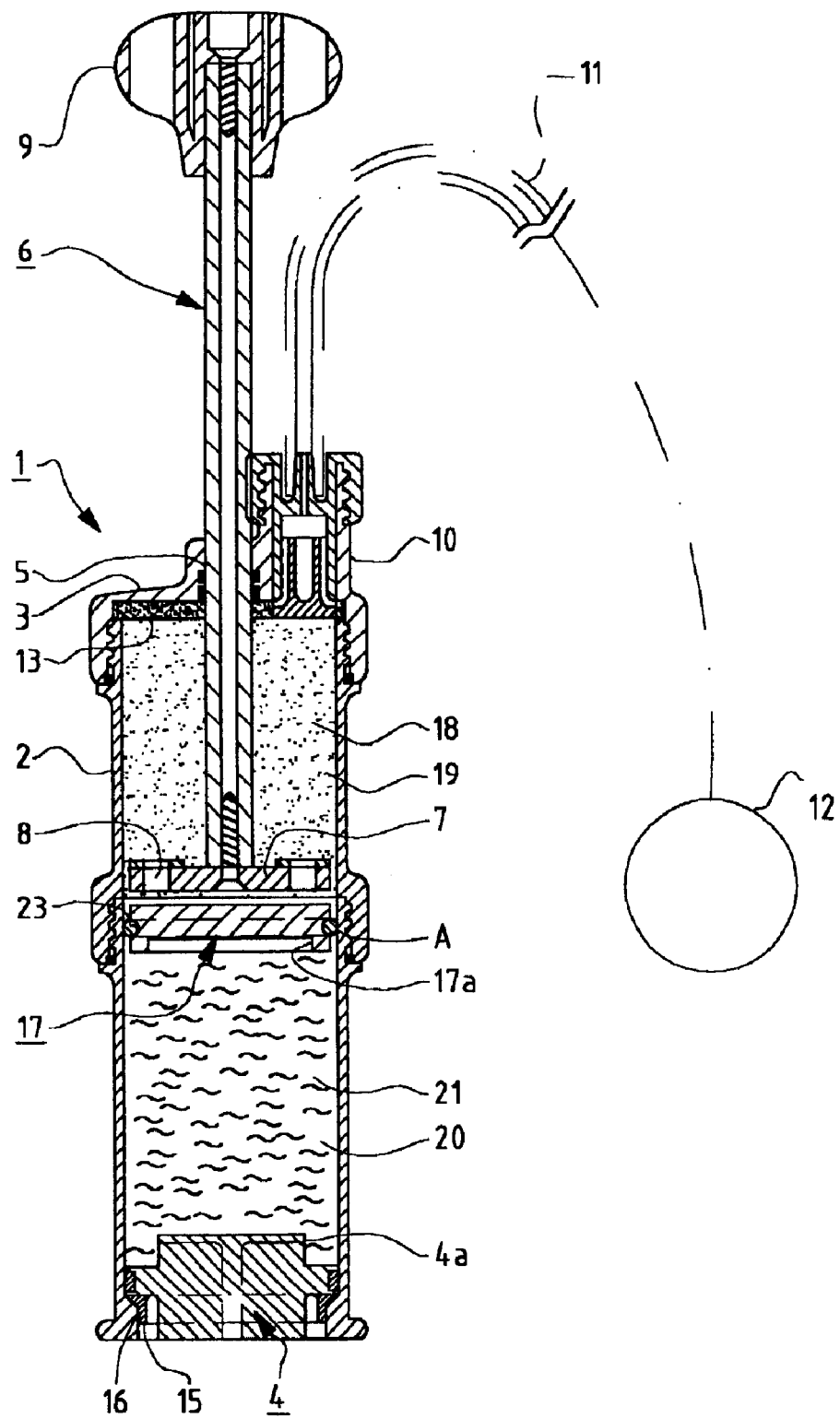
FIG. 1 is a longitudinal section through a mixing device having a device according to the invention.

The mixing device 1 illustrated in the drawings includes a cylindrical member 2 which eventually consists of two parts 2a, 2b which are screwed together. One end opening of the cylindrical member 2 is closed by means of a cap 3 or similar screwed thereon, while the opposite second end opening is closed by means of a closing piston 4 or similar. The cap 3 has a through hole 5 through which a displacement means 6 extends into the cylindrical member 2. The displacement means 6 may include a rod or similar and is sealingly mounted at the cap 3, and it is displaceable in its longitudinal direction and rotatable relative to its longitudinal axis. Inside the cylindrical member 2, the displacement means 6 has at least a mixing member 7 with through openings 8 or similar. By displacing and/or rotating the displacement means 6, it can be used as mixing means for mixing bone cement in the cylindrical member 2 by using the mixing member 7 therefor. The displacement means 6 may, outside the cylindrical member 2, have a handle member 9 which is engaged for displacement and/or rotation of said displacement means 6.

The cap 3 preferably also includes a connecting member 10 for connection of a hose 11 or similar in order to join the cylindrical member 2 to a vacuum generating device 12, e.g. a pump, which is adapted to generate a vacuum in the cylindrical member 2. There may be a filter 13 in the cylindrical member 2 and this filter 13 is adapted to prevent constituents of bone cement from being sucked into the hose 11.

When bone cement shall be discharged from the cylindrical member 2, the hose 11 is released from the connecting member 10 and instead, a discharge member 14, which preferably is tubular, is connected to the connecting member 10 so that bone cement can be discharged through the connecting member 10 and the discharge member 14.

The closing piston 4 may have exterior coupling members 15 or similar, which can cooperate with interior coupling members 16 or similar on the cylindrical member 2 such that the closing piston 4 can be connected to said cylindrical member 2 at said second end opening such that it adheres thereto. The coupling members 15, 16 permit disengagement of the closing piston 4 from the cylindrical member 2 e.g. by rotating said closing piston 4 relative to said cylindrical member 2. After this disengagement, the closing piston 4 may be moved into the cylindrical member 2.

In the cylindrical member 2 there is provided a piston means 17 which divides said cylindrical member 2 into a first space 18 for a pulverulent substance 19, here a polymer, and a second space 20 for a liquid substance 21, here a monomer. The piston means 17 has a groove 22 which extends therearound and which is open in a direction towards a surrounding wall 1a of the mixing device 1. The groove 22 has, in the illustrated embodiment, two parallel or substantially parallel side walls 22a, 22b which are directed inwards towards the central parts of the piston means 17. The groove 22 also has a bottom 22c which in the illustrated embodiment extends in an axial direction relative to the piston means 17 or which extends essentially in this direction. In this groove 22, there is located a sealing ring 23 which preferably has a circular or substantially circular cross-sectional shape and which preferably is elastic. In a normal shape, the sealing ring 23 is in a sealing position A (see FIG. 1) in which it sealingly engages the side walls 22a, 22b of the groove 22 and the wall 1a, which means that the piston means 17 along with the sealing ring 23 sealingly separates the first and second spaces 18, 20 from each other for preventing the polymer 19 and monomer 21 from mixing with each other when mixing should not occur.

For mixing the polymer 19 and monomer 21 with each other, the piston means 17 is pressed by the displacement means 6 in an axial direction B relative to the mixing device 1 towards the second space 20. The sealing ring 23 is thereby loaded by the monomer 21 such that said monomer 21 presses the sealing ring 23 in a direction C into the groove (see FIG. 3) to an opening position D in which it at least partially has disengaged the wall 1a and opened at least a through-flow passage 24 through which the monomer 21 can flow from the second space 20 into the first space 18 (arrow E) to the polymer 19 located therein for mixing therewith.

During said displacement of the piston means 17 in direction B towards the second space 20, it has been found that monomer 21 might be pressed into an inner space 22d in the groove 22 within or behind the sealing ring 23, and in this inner space 22d it can generate or build up a pressure which affects the sealing ring 23 to be unintentionally pressed in a direction F outwards relative to the groove 22 towards the wall 1a, such that it at least temporarily prevents monomer 21 from flowing from the second space 20 to the first space 18.

In order to prevent that the sealing ring 23 is pressed in outwards direction F, i.e. blocking the monomer flow E through the through-flow passage 24, there is in one side wall 22a of the groove 22 provided one or preferably several connecting passages 22e which connect the inner space 22d in the groove 22 with the through-flow passage 24 so that the monomer 21 can not generate said pressure in the inner space 22d but instead, the pressure therein will be substantially equal to the pressure in the through-flow passage 24 when the piston means 17 is displaced.

The connecting passage or passages 22e may be located in the side wall 22a such that they extend from the axially directed outer side of the piston means 17 to the bottom 22c of the groove 22, i.e. such that they connect the through-flow passage 24 and the inner space 22d to each other.

Furthermore, the connecting passage or passages 22e may be located either in the side wall 22a lying closest to the first space 18, but it or they may alternatively be located in the opposite side wall 22b or in both side walls 22a and 22b. There may be a plurality of connecting passages 22e which are provided distributed around the groove 22.

Said means for preventing pressure build-up in the inner space 22d of the groove 22 may of course also be of another type than one or more connecting passages 22e in the side walls 22a and/or 22b of the groove 22. Connecting passages may e.g. be provided in other ways in the piston means 17 and as an alternative to or in combination with connecting passages in the piston means 17 there may be connecting passages in the sealing ring 23.

Before mixing the polymer 19 and monomer 21, the piston means 17 and sealing ring 23 thus define a tight or impermeable partition wall between the first and second spaces 18, 20 and the sealing ring 23 contributes thereto since it in its sealing position A simultaneously engages the side walls 22a, 22b of the groove 22 and the wall 1a. Thus, when the piston means 17 is displaced by the displacement means 6 in direction B towards the second space 20, the sealing ring 23 will be pressed inwards in direction C to its opening position D and thereby release or pass through monomer 21 from the second space 20 to the polymer 19 in the first space 18.

The displacement of the piston means 17 continues until the piston means 17 engages the closing piston 4, whereby all monomer 21 will be located in the same space as the polymer 19. The piston means 17 may have such connecting portions 17a and the closing piston 4 such corresponding connecting portions 4a that the piston means 17 by means of the displacement means 6 can be pressed onto and fixed on the closing piston 4, whereby it is achieved that the piston means 17 can be displaced in the mixing device 1 together with the closing piston 4 as a unit.

When the polymer 19 and monomer 21 are situated in one and same space (consisting of the previous spaces 18 and 20), mixing thereof occurs by means of the displacement means 6, which is displaced in axial direction B and rotated about its longitudinal axis such that its mixing member 7 mix the polymer 19 and monomer 21 with each other. This mixing occurs preferably while generating a vacuum in the mixing device 1 by means of the vacuum generating device 12.

When mixing under vacuum is completed, the generation of vacuum may continue and the closing piston 4 may be released or disengaged from the mixing device 1, whereby said closing piston 4 and the piston means 17 fixed thereon will be sucked into the mixing device 1 by being affected by said vacuum. Thereby, ready mixed bone cement 25 will be collected in the collecting member 26 closest to the connecting member 10. When this is done, the hose 11 to the vacuum generating device 12 may be disconnected from the connecting member 10 and instead, the discharge member 14 can be connected thereto. Finally, a schematically illustrated discharge device 27 may be used for pressing the closing piston 4 along with the piston means 17 in a discharge direction (see FIG. 4) for discharging ready mixed bone cement 25 from the mixing device 1 through the discharge member 14.

The invention is not limited to the embodiment described above, but may vary within the scope of the subsequent claims. Thus, the device may be used at mixing devices for manufacturing completely different medical products than bone cement, whereby naturally the pulverulent substance 19 is another substance than a polymer and the liquid substance 21 another substance than a monomer. The mixing device 1 may be of another construction than shown and this also goes for the construction of the members forming part thereof.

What is claimed is:

1. A mixing device (1) for mixing pulverulent and liquid substances with each other for the manufacture of medical products, the mixing device defining a first space (18) and a second space (20), wherein the pulverulent substance (19) is provided in the first space (18) on one side of a displaceably mounted piston (17) and the liquid substance (21) in is provided in the second space (20) on the opposite side of the piston (17), wherein the piston (17) is displaceable by a displacement means (6), wherein the piston (17) has at least one groove (22) extending around the piston (17), at least one sealing ring (23) being located in the groove (22), wherein the sealing ring (23) is provided to cooperate, in a sealing position (A), with the piston (17) and with a wall (1a) of the mixing device (1), the wall (1a) surrounding the piston (17), whereby the piston (17) and sealing ring (23) sealingly separate the first and second spaces (18, 20) from each other for preventing the pulverulent substance (19) and the liquid substance (21) from mixing with each other when mixing should not occur, and wherein the sealing ring (23) is provided, when loaded by the liquid substance (21) during displacement of the piston (17) in a direction (B) towards the second space (20) containing the liquid, to be pressed inwards in a direction (C) in the groove (22) by the liquid substance (21) and thereby at least partially being brought to leave the sealing position (A) such that the liquid substance (21) may flow into the first space (18) containing the pulverulent substance (19) for mixing therewith, characterized in that at least one connecting passage (22e) is provided to permit flow of the liquid substance (21) out of an inner space (22d) in the groove (22) behind the sealing ring (23), for preventing the liquid substance (21) from generating such a pressure in the inner space (22d) that the pressure presses the sealing ring (23) in a direction (F) outwards relative to the groove (22) towards the surrounding wall (1a) and prevents flow of the liquid substance (21) in a direction (E) from the second space (20) to the first space (18) when the piston (17) is displaced by the displacement means (6) in direction (B) towards the second space (20), the sealing ring (23) leaving the sealing position (A) against the wall (1a) so that the liquid substance (21) may flow between the sealing ring (23) and the wall (1a) into the first space (18) containing the pulverulent substance (19) for mixing therewith.

2. The mixing device (1) according to claim 1, characterized in that the connecting passage (22e) connects the inner space (22d) to a through-flow passage (24) through which the liquid substance (21) can flow from the second space (20) to the first space (18) such that the pressure in the inner space (22d) substantially corresponds with the pressure in the through-flow passage (24) when the piston (17) is displaced.

3. The mixing device (1) according to claim 2, characterized in that the connecting passage (22e) is provided in at least one such inwardly directed side wall (22a) of the groove (22) which extends between the through-flow passage (24) and the inner space (22d).

4. The mixing device (1) according to claim 3, characterized in that the inwardly directed side wall (22a) of the groove (22), provided with the connecting passage (22e), is one of two inwardly directed side walls (22a, 22b) of the groove (22) and situated closest to the first space (18) with the pulverulent substance (19).

5. The mixing device (1) according to claim 2, characterized in that a plurality of connecting passages (22e) are provided distributed around the groove (22).

6. The mixing device (1) according to claim 1, characterized in that the sealing ring (23) is designed to engage, in the sealing position (A), at least one side wall (22a) of the groove (22) provided with the connecting passage (22e), as well as the surrounding wall (1a) of the mixing device (1).

7. The mixing device (1) according to claim 1, characterized in that the sealing ring (23) consists of such elastic material that the sealing ring (23) can be compressed from the sealing position (A) to an opening position (D).

8. The mixing device (1) according to claim 1, characterized in that the first and second spaces (18, 20) form part of the mixing device (1) for manufacturing bone cement (25) and that the pulverulent substance in the first space (18) is a polymer (19) and the liquid substance in the second space (20) is a monomer (21) for the manufacture of the bone cement (25).

9. The mixing device (1) according to claim 8, characterized in that the mixing device (1) includes a connecting member (10) for connection of the mixing device (1) to a vacuum generating device (12) such that a vacuum can be generated in the mixing device (1) during mixing of polymer (19) and monomer (21).

10. The mixing device (1) according to claim 8, characterized in that the mixing device (1) may be connected to a vacuum generating device (12) which can generate such a vacuum in the mixing device (1) that the vacuum affects the piston (17) to move in the mixing device (1) for collection of bone cement (25) in a collecting member (26) of the mixing device (1) from which the bone cement (25) shall be discharged.

11. The mixing device (1) according to claim 8, characterized in that the mixing device (1) includes a closing piston (4) for closing an end opening in the second space (20) for the monomer (21), that the closing piston (4) can be attached to the mixing device (1) in order to be held thereby during mixing of polymer (19) and monomer (21) and that the closing piston (4) is releasable from the mixing device (1) for being displaced therein.

12. The mixing device (1) according to claim 11, characterized in that the piston (17) and the closing piston (4) can be connected to each other so that the closing piston (4) follows the piston (17) if the piston (17) is moved by a vacuum during collection of bone cement (25).

13. The mixing device (1) according to claim 11, characterized in that the piston (17) and the closing piston (4) are displaceable in the mixing device (1) by means of a discharge device (27) for discharging bone cement (25) from the mixing device (1).

14. A mixing device (1) for mixing pulverulent and liquid substances with each other for the manufacture of medical products, the mixing device defining a first space (18) and a second space (20), wherein the pulverulent substance (19) is provided in the a first space (18) on one side of a displaceably mounted piston (17) and the liquid substance (21) in is provided in the second space (20) on the opposite side of the piston (17), wherein the piston (17) is displaceable by a displacement means (6), wherein the piston (17) has at least one groove (22) extending around the piston (17), at least one sealing ring (23) being located in the groove (22), wherein the sealing ring (23) is provided to cooperate, in a sealing position (A), with the piston (17) and with a wall (1a) of the mixing device (1), the wall (1a) surrounding the piston (17), whereby the piston (17) and sealing ring (23) sealingly separate the first and second spaces (18, 20) from each other for preventing the pulverulent substance (19) and the liquid substance (21) from mixing with each other when mixing should not occur, and wherein the sealing ring (23) is provided, when loaded by the liquid substance (21) during displacement of the piston (17) in a direction (B) towards the second space (20) containing the liquid, to be pressed inwards in a direction (C) in the groove by the liquid substance (21) and thereby at least partially being brought to leave the sealing position (A) such that the liquid substance (21) may flow into the first space (18) containing the pulverulent substance (19) for mixing therewith, characterized in that at least one connecting passage (22e) is provided to permit flow of the liquid substance (21) out of an inner space (22d) in the groove (22) behind the sealing ring (23), for preventing the liquid substance (21) from generating such a pressure in the inner space (22d) that the pressure presses the sealing ring (23) in a direction (F) outwards relative to the groove (22) towards the surrounding wall (1a) and prevents flow of the liquid substance (21) in a direction (E) from the second space (20) to the first space (18) when the piston (17) is displaced by the displacement means (6) in direction (B) towards the second space (20), the mixing device (1) including a movable mixing means which is adapted for mixing polymer (19) and monomer (21) and which is made up of the displacement means (6).

* * * * *

UNITED STATES PATENT AND TRADEMARK OFFICE
CERTIFICATE OF CORRECTION

PATENT NO. : 6,871,996 B2
DATED : March 29, 2005
INVENTOR(S) : Ernst Jonsson

It is certified that error appears in the above-identified patent and that said Letters Patent is hereby corrected as shown below:

Column 4,
Line 58, before "is" delete "in".

Column 6,
Line 45, before "first" delete "a" (1st occurrence).
Line 46, before "is" delete "in".

Signed and Sealed this

Sixteenth Day of August, 2005

JON W. DUDAS
*Director of the United States Patent and Trademark Office*